United States Patent [19]

Jackman et al.

[11] Patent Number: 4,954,627

[45] Date of Patent: Sep. 4, 1990

[54] PROCESS FOR DESULFURIZATION OF ISOTHIOUREAS AND ISOTHIOAMIDES

[75] Inventors: Dennis E. Jackman, Prairie Village; John G. Morgan, Stilwell, both of Kans.

[73] Assignee: Mobay Corporation, Pittsburgh, Pa.

[21] Appl. No.: 277,739

[22] Filed: Nov. 30, 1988

[51] Int. Cl.$^5$ ............................................. C07D 253/00
[52] U.S. Cl. ............................... 544/182; 548/165; 558/1; 558/4
[58] Field of Search ...................... 544/182; 548/165; 558/1, 4

[56]  References Cited

PUBLICATIONS

Jackman et al., "A New Method for the Synthesis of Heterocyclic S-Alkyl Thiolactams", Chemical Abstracts, vol. 109, #128959f (1988).

Barlow et al., Journal of the American Chemical Society, vol. 78, pp. 1258–1259, 1956.

Kim et al., Novel Desulfurization of Thiocarbonyl Compounds Into Their Carbonyl Compounds with Tertiary Butyl Thionitrate, vol. 28, pp. 1669–1670, 1987, Tetrahedron Letters.

*Primary Examiner*—Mukund J. Shah
*Assistant Examiner*—C. L. Cseh
*Attorney, Agent, or Firm*—Joseph C. Gil; Lyndanne M. Whalen

[57]  ABSTRACT

The present invention is directed to a process for desulfurizing a compound selected from isothioureas and isothioamides comprising heating the compound to be desulfurized in the presence of a mercaptanol to produce the corresponding desulfurized keto compound.

6 Claims, No Drawings

PROCESS FOR DESULFURIZATION OF ISOTHIOUREAS AND ISOTHIOAMIDES

BACKGROUND OF THE INVENTION

The present invention relates to a process for the desulfurization of isothioureas and isothioamides.

Most of the known procedures for converting thioureas or isothioureas to ureas involve hydrolysis with strong acid (See, e.g., Barlow et al, *Journal of the American Chemical Society*, Col. 78, pages 1258–1259) or oxidation (See, e.g., Kim et al, Novel Desulfurization of Thiocarbonyl Compounds Into Their Carbonyl Compounds With Tertiary Butyl Thionitrate, *Tetrahedron Letters*, Vol. 28, No. 15, pages 1669–1670 (1987)).

These procedures are not however suitable for all thioureas and isothioureas. More specifically, acid hydrolysis is clearly inappropriate for thioureas and isothioureas which are sensitive to acids. Oxidation procedures are obviously unsuitable for thioureas and isothioureas containing other oxidizable groups (i.e, in addition to the thiourea group).

It would therefore be advantageous to be able to desulfurize acid sensitive isothioureas and isothioamides and/or isothioureas and isothioamides containing more than one oxidizable group.

SUMMARY OF THE INVENTION

It is an object of the present invention to provide a process for desulfurizing compounds such as isothioureas and isothioamides.

It is also an object of the present invention to provide a process for desulfurizing such compounds which are acid sensitive and/or which contain more than one oxidizable substituent.

These and other objects which will be apparent to those skilled in the art are accomplished by heating an isothiourea and isothioamide in the presence of a mercaptanol to produce the corresponding desulfurized keto compound.

DETAILED DESCRIPTION OF THE INVENTION

The present invention relates to a desulfurization process in which an isothiourea or isothioamide is heated in the presence of a mercaptanol to produce the corresponding desulfurized keto compound.

Any of the known isothioureas may be used in the practice of the present invention. Such isothioureas may be produced, for example, by reacting an alkylhalide and a thiourea. Examples of suitable isothioureas include: alkylthiotriazinones and 2-alkylthiopyrimidones. Examples of preferred isothioureas are "metribuzin" (4-amino-6-t-butyl-3-methylthio-1,2,4-triazin-5(4H)one.

Any of the known isothioamides may also be used as a starting material in the process of the present invention. Examples of suitable isothioamides include mercaptothiazoles, 6-methythionicotinamide, 6-alkylthiopurines. Preferred isothioamides are 2-alkylthiomercaptothiazoles, alkylthiomercaptothiadiazoles and alkylthiobenzothiazoles.

The mercaptanol used in the process of the present invention may be any compound represented by the formula

HS—R—OH in which R represents an alkyl, cycloalkyl, substituted cycloalkyl, aromatic or substituted aromatic radical.

Examples of appropriate mercaptanols include: mercaptoethanol, 2-mercaptopropanol and 3-mercaptopropanol. Preferred mercaptanols are mercaptoethanol and 2-mercaptopropanol.

The desulfurization may be carried out in the presence of an appropriate solvent (e.g., toluene, xylene, excess mercaptoalkanol) and/or catalyst (e.g., KOH, $K_2C)_3$, toluenesulfonic acid).

The desulfurization is generally carried out at a temperature of from 50° to 160°, preferably from 70° to 145°, and most preferably from 75° to 140°.

Having thus described our invention, the following Examples are given as being illustrative thereof.

EXAMPLES

Example 1

1 gram of metribuzin represented by the formula

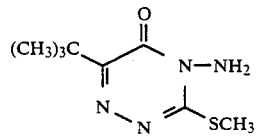

was heated at 125° C. for one hour in the presence of mercaptoethanol to obtain the product

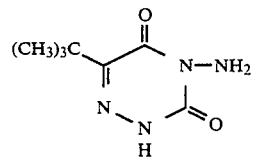

in a yield of 830 mg (97% of theoretical).

Example 2

1.0 gram of 2-methyl-mercaptobenzothiazole was heated to 130° C. for 12 hours in the presence of 6 grams of mercaptoethanol and a catalytic amount of KOH (50 mg) to obtain 2-oxobenzothiazole. This reaction is represented by the equation:

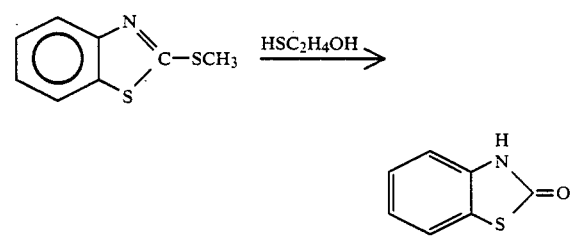

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the desulfurization of a compound selected from isothioureas and isothioamides comprising heating the compound to be desulfurized in the presence of a mercaptanol to produce the corresponding desulfurized keto compound.

2. The process of claim 1 in which an isothiourea is heated in the presence of mercaptoethanol.

3. The process of claim 1 in which an isothioamide is heated in the presence of mercaptoethanol.

4. The process of claim 1 in which a mercaptothiazole is heated in the presence of mercaptoethanol.

5. The process of claim 1 in which metribuzin is heated in the presence of mercaptoethanol.

6. The process of claim 1 in which 2-methylmercaptobenzothiazole is heated in the presence of mercaptoethanol.

* * * * *